United States Patent [19]

Farthing et al.

[11] 4,167,526

[45] Sep. 11, 1979

[54] PROCESS FOR PREPARING N,N,N',N'-TETRAPHENYLDIAMINOMETHANE

[75] Inventors: Alan C. Farthing; Eric S. Nicholson, both of Manchester, England

[73] Assignee: Imperial Chemical Industries Limited, London, England

[21] Appl. No.: 524,947

[22] Filed: Nov. 18, 1974

[30] Foreign Application Priority Data

Nov. 29, 1973 [GB] United Kingdom ............... 55419/73

[51] Int. Cl.$^2$ .......................................... C07C 91/16
[52] U.S. Cl. ............................. 260/570.5 P; 252/401; 260/45.9 QA; 260/809
[58] Field of Search ........................ 160/570.5 P, 576

[56] References Cited

U.S. PATENT DOCUMENTS 1,890,916  12/1932  Semon ................................ 260/884

OTHER PUBLICATIONS

Craig, "Journal American Chemical Society", vol. 55, pp 3723-3727 (1933).
Walker, "Formaldehyde", 3rd Ed., p. 632 (1964).

*Primary Examiner*—Robert V. Hines
*Attorney, Agent, or Firm*—Cushman, Darby & Cushman

[57] ABSTRACT

N,N,N',N'-tetraphenyldiaminomethane, antioxidant for rubber, is prepared by reaction of 2 molar proportions of diphenylamine and 0.8–1.3 molar proportions of formaldehyde at room temperature. The reaction may be carried out in a storage container, for example a thermoplastic container which, holding the tetraphenyldiamonomethane, can be added to and will blend into a rubber mix.

8 Claims, No Drawings

PROCESS FOR PREPARING N,N,N',N'-TETRAPHENYLDIAMINOMETHANE

This invention relates to an improved process for the preparation of N,N,N',N'-tetraphenyldiaminomethane.

Tetraphenyldiaminomethane is useful as an antioxidant for e.g. rubber and may be prepared by heating equimolar amounts of diphenylamine and formalin in an inert solvent such as boiling benzene. The product contains much unreacted diphenylamine and a lengthy purification is required to obtain the desired product is solid form.

Alternatively it may be prepared by heating diphenylamine and formaldehyde in the absence of solvent at e.g. 110° C. for several hours. The product obtained is a viscous liquid which gradually changes to a hard solid on storage. This change in physical form, and the form itself at any stage, make it difficult to handle the product for use in rubber. The product may be converted into a more attractive powder form by purification, for example by crystallisation, but there is a significant loss of product and the process is uneconomical. Alternatively the product may be broken down to a powder by milling but this is an undesirable additional expense.

It has now been found that if the reaction between diphenylamine and formaldehyde is carried out at significantly lower temperatures tetraphenyldiaminomethane is obtained in high yield as a white powder or small aggregates which may be handled easily.

According to the invention there is provided a process for the manufacture of N,N,N',N'-tetraphenyldiaminomethane which comprises reacting 2 molar proportions of diphenylamine with from 0.8 to 1.3 molar proportions of formaldehyde at a temperature below the melting point of the reaction mixture.

The process may be carried out simply by mixing the diphenylamine in any convenient form, e.g. powder or flake, with the formaldehyde and keeping the mixture until the reaction has proceeded to the desired degree. The time required for reaction will depend upon the temperature and the proportion of formaldehyde, for example after 7 weeks at 21°–23° C. using 1.3 molar proportions of formaldehyde for 2 molar proportions of diphenylamine only 9% of unreacted diphenylamine remained.

The formaldehyde may be used as aqueous solution, conveniently the commercially available 37% by weight aqueous solution known as formalin. Alternatively a source of free formaldehyde under the reaction conditions may be used, for example paraformaldehyde.

The formaldehyde is preferably used in amount between 1 and 1.3 molar proportions for each 2 molar proportions of diphenylamine. Amounts outside this range may be used but less formaldehyde will increase the diphenylamine content of the product and the reaction may proceed more slowly. More formaldehyde may afford a product containing undesirable free formaldehyde or which may yield it on heating.

The preferred reaction temperatures are between 0° and 45° C. Temperatures below this range may be used but the reaction is generally undesirably slow. Higher temperatures may lead to a less easily handled product and less complete conversion to the product.

When paraformaldehyde is used as source of formaldehyde the diphenylamine retains its form, for example as powder or flake, but is gradually converted into tetraphenyldiaminomethane similarly as powder or flake. When formalin, or paraform and water, is used the diphenylamine, whether in powder or flake form, passes through a putty-like stage before yielding tetraphenyldiaminomethane in the form of small lumps. Tetraphenyldiaminomethane as obtained in any of these forms is easily handled and convenient to weigh out and incorporate into rubber mixes.

The conversion of diphenylamine to tetraphenyldiaminomethane when using suitable proportions of reactants will approach 100% after sufficient time. However for use as an antioxidant the crude product will normally be satisfactory even if containing up to 10% of diphenylamine.

The speed of reaction is considerably increased by the presence of water, which may be added when paraform is used or which is present in formalin when used as a source of formaldehyde. The presence of water is especially desirable when using diphenylamine flake and paraform with which the final stage of reaction is slow.

The speed of reaction is also increased by catalytic amounts of certain solvents, for example liquids of high dielectric constant, such as nitrobenzene, formamide, ethanol, acetone, ethylene glycol, acetamide, methylacetamide, methylformamide, dimethylformamide, pyridine, alkylpyridines, which may be used alone or in combination in addition to or instead of water.

In order to avoid the use of expensive plant in which to carry out the manufacture it is advantageous to mix the diphenylamine and formaldehyde and charge the mixture to the container in which the product is to be stored and transported and, after a sufficient time to bring about the necessary extent of reaction, to market the product in that container. For example the reaction mixture may be charged to conventional containers such as metal drums or sacks lined with polyethylene from which after the necessary period of storage the user may take the amount desired.

Alternatively, if the container is made of a material which is compatible with the rubber or thermoplastic material in which the tetraphenyldiaminomethane is to be used, and the construction of the container is such that the container will be ruptured while being added to e.g. rubber in conventional blending apparatus, further advantage is obtained in that it is no longer necessary to take the material from its container before use. The container holding the tetraphenyldiaminomethane may be added to a rubber or thermoplastic polymer while this is being plasticised by heat and mechanical working in a conventional mixing apparatus, for example a two roll mill or internal mixer. The operation of the mixing apparatus will rupture the container and blend or disperse both the tetraphenyldiaminomethane and the material of the container into the rubber or thermoplastic polymer.

Suitable such container materials are thermoplastic materials such as low density polyethylene, ethylene/vinyl acetate copolymers, thermoplastic rubbers of the styrene/butadiene or styrene/isoprene block copolymer type and polyisobutylene.

By suitable choice of materials containers may be obtained from which any water added or formed in the process of the invention or solvents added may at least in part diffuse through the container walls during storage and evaporate into the atmosphere.

The containers may be of any shape convenient for manufacture, filling, sealing, storing, transporting and handling, and will normally contain amounts of tetraphenyldiaminomethane or ingredients therefrom which are convenient for use in the rubber industry, for example from 0.05 to 2 Kg. and preferably from 0.1 to 0.5 Kg. It is convenient to fill each container with the same amount of ingredients so that the amount of antioxidant to be added to e.g. the rubber can be provided simply by taking the appropriate number of containers.

The containers may be performed and then filled with the reaction mixture in any conventional manner, but it is convenient to form, fill and seal, for example by the application of heat and pressure, the containers in essentially one operation in machines which are well-known and used for example in the packaging of foodstuffs. The containers may be separate from each other or may for example be joined end-to-end to form chains from which individual containers may be separated as desired by cutting across the joining member.

The operation of the process in such containers, the containers when filled with the product of the process of the invention, and the use of such filled containers in rubber and plastics are further features of the invention.

The invention is illustrated but not limited by the following examples in which all parts and percentages are by weight unless otherwise stated.

EXAMPLE 1

168 Parts of diphenylamine were ground in a coffee grinder for approximately 20 seconds, 15 parts of paraformaldehyde were added and the mixture then ground for a further 20 seconds. The ground material was then poured into a polyethylene bag which was then sealed. Analysis of the contents by gas liquid chromatography after 59 days storage at room temperature gave 15.6% of diphenylamine and 81.5% of N,N,N',N'-tetraphenyldiaminomethane. The product was in the form of a coarse powder varying in colour from white to cream depending on the quality of the diphenylamine.

EXAMPLE 2

The procedure of Example 1 was repeated using 168 parts of diphenylamine and 19.5 parts of paraformaldehyde and the reaction mixture analysed at intervals of time. The content of diphenylamine found was as follows.

| Time Days | Diphenylamine content % |
|---|---|
| 0 | 89 |
| 14 | 39 |
| 28 | 26.4 |
| 34 | 22 |
| 43 | 10.9 |
| 49 | 8.1 |
| 57 | 4.8 |
| 59 | 2.4 |

The product after 59 days was a coarse powder containing 94.2% of N,N,N',N'-tetraphenyldiaminomethane.

EXAMPLE 3

56 Parts of diphenylamine in flake form and 16.3 parts of formalin (containing 36.5% of formaldehyde) were poured into a polyethylene bag which was then sealed. Analysis after storage at room temperature for 37 days gave 3.5% of diphenylamine and 85.3% of N,N,N',N'-tetraphenyldiaminomethane. The product was in the form of small lumps.

EXAMPLE 4

56 Parts of diphenylamine were ground in a coffee grinder as in Example 1. 6.5 Parts of paraformaldehyde were added and the mixture ground for a further 20 seconds. The ground material was then poured into a polyethylene bag. 7.5 Parts of water were poured into the bag which was then sealed. After storage at room temperature for 37 days analysis showed 85.7% of N,N,N',N'-tetraphenyldiaminomethane and less than 0.1% of diphenylamine. The product was in the form of a coarse powder.

EXAMPLE 5

56 Parts of diphenylamine and 6.5 parts of paraformaldehyde were ground and poured into a polyethylene bag as in Example 4. 0.05 Parts of nitrobenzene were then poured into the bag which was then sealed. After storage at room temperature for 29 days analysis showed 87.7% of N,N,N',N'-tetraphenyldiaminomethane and 7.6% of diphenylamine. The product was in the form of a coarse powder.

EXAMPLE 6

56 Parts of diphenylamine and 6.5 parts of paraformaldehyde were ground and poured into a polyethylene bag as in Example 4. 0.73 Parts of N,N-dimethyl formamide were added to the bag which was then sealed. After storage at room temperature for 52 days analysis showed 84.8% of N,N,N',N'-tetraphenyldiaminomethane and 8.9% of diphenylamine to be present. The product was in the form of a coarse powder.

EXAMPLE 7

56 Parts of diphenylamine and 6.5 parts of paraformaldehyde were ground and poured into a polyethylene bag as in Example 4. 2.5 Parts of water and 0.8 parts nitrobenzene were then poured into the bag after which it was sealed. After storage at room temperature for 32 days analysis showed 90% of N,N,N',N'-tetraphenyldiaminomethane and 0.6% of diphenylamine to be present. The product was in the form of a coarse powder.

EXAMPLE 8

56 Parts of diphenylamine and 6.5 parts of paraformaldehyde were ground and poured into a polyethylene bag as in Example 4. 0.06 Parts of N-methyl formamide and 1.1 parts of nitrobenzene were then poured into the bag after which it was sealed. After storage at room temperature for 47 days analysis showed 95% of N,N,N',N'-tetraphenyldiaminomethane and 1.3% of diphenylamine to be present. The product was in the form of a coarse powder.

We claim:

1. A process for the manufacture of N,N,N',N'-tetraphenyldiaminomethane which comprises reacting 2 molar proportions of diphenylamine with from 0.8 to 1.3 molar proportions of formaldehyde at a temperature below the melting point of the reaction mixture.

2. A process as claimed in claim 1 in which the temperature is between 0° and 45° C.

3. A process as claimed in claim 1 in which there is used from 1.0 to 1.3 molar proportions of formaldehyde.

4. A process as claimed in claim 1 in which the formaldehyde is used in the form of paraformaldehyde.

5. A process as claimed in claim 1 in which water is present.

6. A process as claimed in claim 1 which is carried in a container in which the product is to be stored and marketed.

7. A process as claimed in claim 6 wherein the container is made of polyethylene.

8. A process as claimed in claim 6 wherein the container is made of an ethylene-vinyl acetate copolymer.

* * * * *